(12) United States Patent
Grushin

(10) Patent No.: US 7,202,388 B2
(45) Date of Patent: Apr. 10, 2007

(54) PROCESSES FOR PREPARING FLUOROARENES FROM HALOARENES

(75) Inventor: Vladimir Grushin, Hockessin, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 11/244,980

(22) Filed: Oct. 5, 2005

(65) Prior Publication Data

US 2006/0074261 A1   Apr. 6, 2006

Related U.S. Application Data

(60) Provisional application No. 60/616,263, filed on Oct. 6, 2004.

(51) Int. Cl.
*C07C 22/00* (2006.01)
(52) U.S. Cl. .................. 570/147; 570/170
(58) Field of Classification Search ............ 570/171, 570/147
See application file for complete search history.

(56) References Cited

U.S. PATENT DOCUMENTS

| | | | |
|---|---|---|---|
| 3,398,203 A | 8/1968 | Olson | |
| 4,394,527 A | 7/1983 | Fischer, Jr. et al. | |
| 5,315,043 A | 5/1994 | Fernandez et al. | |
| 5,756,834 A | 5/1998 | Pasenok et al. | |
| 5,965,775 A | 10/1999 | Pfirmann et al. | |
| 6,087,543 A | 7/2000 | Subramanian | |
| 6,166,273 A | 12/2000 | Subramanian | |
| 6,469,224 B1 | 10/2002 | Nobori et al. | |
| 6,784,327 B2 * | 8/2004 | Yoneda et al. | 570/176 |

FOREIGN PATENT DOCUMENTS

WO   WO 01/096267 A1   12/2001

OTHER PUBLICATIONS

Vlasov et al., Nucleophilic Substitution of the Nitro Group, Fluorine And Chlorine in Aromatic Compounds, Russian Chem. Review, 2003, vol. 72:681-703.
Adams et al., Nucleophilic Routes to Selectively Fluorinated Aromatics, Chem. Soc. Rev., 1999, vol. 28:225-231.
V. Grushin et.al., Palladium Fluoride Complexex: One More Step Toward Metal-Mediated C-F Bond Formation, Chem. Eur. J., 2002, vol. 8:1006-1014.
Bunnett et al., Aromatic Nucleophilic Substitution Reactions, Chem. Review, 1951, pp. 273-412.
Kageyama et. al., Sulfonyl Chloride as A Disposable Electron Withdrawing Substituent in Halex Fluorinations, Journal of Fluorine Chemistry, 2000, vol. 101:85-89.
Plevey et. al., Fluorination with Complex Metal Fluorides Part II. The Fluorination of Benzene, Tetrahydrofuran and Cyclohexanone with Silver Difuoride and Potassium Tetrafluoroargentate, Journal of Fluorine Chemistry, 1973, vol. 3:259-266.
Hansch et. al., Aromatic Substituent Constants for Structure-Activity Correlations, Journal of Medicinal Chemistry, 1973, vol. 16:1207-1216.
McDaniel et. al., An Extended Table of Hammett Substituent Constants Based on the Ionization of Substituted Benzoic Acids, 1957, vol. 23:420-427.
Ebert et. al., Direct Formation of (Haloaryl) Copper Nucleophiles from Haloiodobenzenes and Active Copper, J. Org. Chem., 1995, vol. 60:2361-2364.

* cited by examiner

*Primary Examiner*—Samuel Barts

(57) ABSTRACT

Processes for preparing fluoroarenes are provided. The processes include contacting a compound having an unactivated aryl group with a source of fluoride or bifluoride in the presence of a transition metal a ligand.

8 Claims, No Drawings

PROCESSES FOR PREPARING FLUOROARENES FROM HALOARENES

FIELD OF INVENTION

The invention is directed to processes for the preparation of fluoroarenes from nonactivated haloarenes.

BACKGROUND

Selectively fluorinated aromatic compounds are often biologically active and can be used as active components of many drugs and agrochemicals. Nucleophilic substitution of iodide, bromide, and chloride in readily available haloarenes with fluoride can be the easiest, safest, and most efficient way to make fluoroaromatics. Vlasov et al (Russian Chem. Review, 2003 72(8), 681–703) and Adams et al (Chem. Soc. Rev., 1999, 28, 225–231) reviewed fluorination methods by halogen and nitro exchange, but in all cases the aromatic compound was activated toward the displacement with fluoride by other moieties on the ring.

Existing methods to fluorinate nonactivated aromatic rings are expensive, impractical and yield low amounts of the desired compounds. The best-known method for fluorination of nonactivated aromatic rings is the Balz-Schiemann reaction, which uses expensive, toxic and potentially explosive diazonium salts at elevated temperatures. Other methods use the even more toxic thallium, mercury, and lead compounds, or costly iodonium salts (Grushin, V., Chem. Eur. J., 2002, 8, No. 5). In U.S. Pat. No. 6,166,273 benzene was fluorinated by the non-catalytic reaction with $CuF_2$ to producing Cu metal, but this reaction was run only in the gas phase.

What is needed, then, is a better and safer catalytic method for the introduction of fluorine into the aromatic ring, especially of nonactivated aromatic compounds. The applicant has discovered a new method for the preparation of fluoroarenes via the use of copper (II) fluoride in the presence of some bidentate tertiary amine ligands.

SUMMARY OF THE INVENTION

The invention is directed to a fluorination process comprising: contacting a compound having an unactivated aryl group substituted with one or more of X, wherein X is I, Br, Cl, triflate, or tosylate with a source of fluoride or bifluoride, a transition metal, and a ligand; wherein the contacting is carried out in a solvent for a time sufficient to replace one or more of X with F.

DETAILED DESCRIPTION OF THE INVENTION

The invention is directed to a process for the fluorination of an aromatic compound, comprising contacting a compound having an aryl group substituted with one or more of X, wherein X is I, Br, Cl, triflate ($—OSO_2CF_3$), or tosylate ($—OSO_2C_6H_4CH_3$), with a source of fluoride, bifluoride or a mixture of both, a transition metal, and a ligand, for a time sufficient to replace one or more of X with F. The contact is carried out with all reactants either dissolved, slurried or otherwise contained in a liquid phase. The method is most useful for the synthesis of aryl fluorides from unactivated aryl compounds.

Preferably the aryl group is substituted with optionally substituted aryl, hydrogen, optionally substituted alkyl, aryloxy, alkoxy, amine, and hydroxyl; more preferably benzene or naphthalene, optionally substituted with one or more of bromo and iodo.

The source of fluoride or bifluoride can be, for example, NaF, KF, RbF, CsF, AgF, TlF, $NaHF_2$, and $KHF_2$. The transition metal can be selected from Cu, Ag, Au, Fe, Co, Ni, Ru, Rh, Pd, Os, Ir, Pt, and Re. The ligand can be N,N,N',N'-tetramethylethylenediamine, N,N,N',N'-tetraethylethylenediamine, or N,N,N',N'-tetramethylphenylenediamine. The solvent can be selected from hexamethylphosphoramide, tetramethylene sulfone, N-methyl-2-pyrrolidone, and diglyme, and can also be an aprotic solvent.

By "unactivated aryl" is meant an aryl group that is unsubstituted or substituted only with one or more functional groups that do not activate the nucleophilic substitution at a carbon atom of the aryl group. Unactivated aryl groups are well known to those skilled in the art and are disclose, for example, in J. March, Advanced Organic Chemistry, $2^{nd}$ Edition, McGraw-Hill, NY, 1977, pg. 591–595; J. Miller, Aromatic Nucleophilic Substitution, Elsevier, London, 1968, 408 pp.; and F. Terrier, Nucleophilic Aromatic Displacement: The Influence of the Nitro Group, VCH, New York, 1991, 460 pp. Such a non-activating group is, in general, an electron donor or a weak electron acceptor. Examples of non-activating groups include, but are not limited to, hydrogen, fluorine, chlorine, bromine, iodine, optionally substituted alkyl, aryl, alkoxy, and aryloxy, amine, dialkylamine, hydroxyl, acyl, and aroyl. An activating group is a functional group that activates the aromatic ring toward nucleophilic substitution, and, in general, is a strong electron acceptor. Examples of activating groups include, but are not limited to, nitro, cyano, perfluoroalkyl, and other strongly electron-withdrawing groups. Weaker electron-acceptors, such as chlorine, can also activate the aromatic ring, provided the ring bears several of them. An example of such activation is the synthesis of hexafluorobenzene from hexachlorobenzene and KF via the Halex Process; see, for example B. Langlois et al Ind. Chem. Libr. 1996, 8, 244.

"Alkyl" means an alkyl group up to and including 12 carbons, and can be linear or branched. Common examples of such alkyl groups include, but are not limited to, methyl, ethyl, propyl, isopropyl, butyl, s-butyl, isobutyl, pentyl, neopentyl, hexyl, heptyl, isoheptyl, 2-ethylhexyl, cyclohexyl and octyl.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl). Common examples include, but are not limited to, benzene, biphenyl, terphenyl, naphthalene, phenyl naphthalene, and naphthylbenzene. Also included are charged aromatic carbocyclics such as the cyclopentadienyl anion and the cycloheptatrienyl cation.

By aryl is also meant heteroaryl groups where heteroaryl is defined as 5-, 6-, or 7-membered aromatic ring systems having at least one heteroatom selected from the group consisting of nitrogen, oxygen and sulfur. Examples of heteroaryl groups include, but are not limited to, are pyridyl, pyrimidinyl, pyrrolyl, pyrazolyl, pyrazinyl, pyridazinyl, oxazolyl, furanyl, quinolinyl, isoquinolinyl, thiazolyl, and thienyl.

In the processes of the instant invention, the aryl group is optionally substituted with a non-activating group. Optionally substituted", as used herein, means a group may be substituted and may contain one or more substituent groups that do not cause the compound to be unstable or unsuitable for the use or reaction intended, and are not considered "activating" as defined above.

The choice of solvent is not critical provided the solvent is not detrimental to catalyst, reactant and product. The solvent may be a mixture, and may itself be the starting compound. Suitable solvents can include, but are not limited to, hexamethylphosphoramide, tetramethylene sulfone, N-methyl-2-pyrrolidone, diglyme, pentane, hexane, benzene, toluene, methylene chloride, carbon tetrachloride, chloroform, tetrahydrofuran, dimethylsulfoxide and dimethylformamide. Preferred solvents include aprotic solvents, which may be polar or non-polar but, in either case, do not contain acidic hydrogens and therefore are not capable of hydrogen bonding with solutes. Preferably the solvent is anhydrous.

By "ligand" is meant a compound that coordinates to a metal. Ligands and coordination chemistry is well-known in the art; see, for example, Coordination Compounds, Kirk-Othmer Encyclopedia of Chemical Technology, John Wiley & Sons, Inc., DOI: 10.1002/0471238961.0315151801180308.a01.pub2. Ligands are Lewis bases with at least one lone electron pair available for coordination to the metal. The ligand may be neutral or charged, and may be unidentate, bidentate, or higher. The ligand can be selected depending upon the particular metal or metals used. Suitable ligands include organic compounds containing at least functional group containing nitrogen, oxygen, phosphorus, sulfur, and arsenic. Examples of such organic compounds include amine compounds such as N,N,N',N',-tetramethylethylenediamine. Other suitable ligands include mono-, di-, and polydentate amines, mono-, di-, and polydentate phosphines, and also mixed ligands containing two or more different heteroatoms (e.g., N, O, P, S, and As), in various combinations, capable of coordinating to a Lewis acid. One or more ligands, either the same or different, may be used.

By "transition metal" it is meant an element in groups 3 through 12 of the Periodic Table of the Elements. The metal can be in the form of a salt, complex, or elemental, and can be dissolved or slurried in the solvent. It may also be supported on a suitable inert support. The transition metal compound may also function as the source of fluoride or bifluoride, as described below. One or more transition metals, either the same or different, may be used in the instant invention By "source of fluoride or bifluoride" it is meant a compound that will provide fluoride or bifluoride ($HF_2$—) ions under reaction conditions. Suitable sources include, but are not limited to, metal fluoride salts such as NaF, KF, RbF, CsF, AgF, TlF, $NaHF_2$, and $KHF_2$. The source of fluoride can be used in the presence of a phase-transfer agent to enhance the solubility of the fluoride in the reaction medium. Examples of phase-transfer agents include, but are not limited to crown-ethers, cryptates, and onium salts, such as tertiary ammonium, phosphonium, and phosphazenium salts. The phase-transfer agents can be used in catalytic (less than 1 equivalent per fluoride source) or stoichiometric (more than 1 equivalent per fluoride source) quantities.

The process can be run at a wide range of temperatures provided that the temperature is not so high as to result in decomposition of the reactants or products, and under any atmosphere inert to the reactants and products. Preferably the atmosphere is essentially free of moisture. The reactants and products can be dissolved or slurried in the solvent. The temperature will depend on choice of solvent, but can be from about 20° C. to about 200° C., or from about 60° C. to about 200° C.

The process can be run at any pressure but preferably at about atmospheric.

The product can be separated and/or purified by any variety of techniques known in the art, such as but not limited to extraction, crystallization, and distillation.

EXAMPLES

Materials and Methods

All solvents and reagents were thoroughly dried prior to use. Copper (II) fluoride (99%+, Acros, Morris Plains, N.J.) was used as received. All reactions were carried out in Nalgene® tubes, under rigorously anhydrous conditions. A Bruker Avance DRX 400 instrument was used for recording $^{19}F$ NMR data. 2-Iodonaphthalene was prepared as described in: Suzuki, H.; Kondo, A.; Inouye, M.; Ogawa, T. Synthesis 1986, 121, and purified by vacuum sublimation.

| Abbreviations: | |
|---|---|
| HMPA | hexamethylphosphoramide |
| Sulfolane | tetramethylene sulfone |
| NMP | N-methyl-2-pyrrolidone |
| TMEDA | N,N,N',N'-tetramethylethylenediamine |

Example 1

A mixture of 2-iodonaphthalene (0.10 g), copper (II) fluoride (0.04 g), TMEDA (0.31 mL), and HMPA (1.5 mL) was vigorously stirred at 180° C. for 3 hrs. After the mixture was allowed to cool to room temperature, water (5 mL) and hexanes (2 mL) were added. The mixture was vigorously shaken for extraction into the hexane phase, which was then filtered through a short silica gel plug. Analysis of the filtrate by $^{19}F$ NMR indicated the formation of 2-fluoronaphtalene. The characteristic multiplet at −116 ppm was identical with that observed for an authentic sample of 2-fluoronaphtalene (Aldrich, St. Louis, Mo.).

Example 2

A mixture of iodobenzene (0.46 mL), copper (II) fluoride (0.28 g), TMEDA (0.83 mL), and HMPA (2 mL) was vigorously stirred at 150° C. for 2 hrs and then at 180° C. for 2 hrs 10 min. After the mixture was allowed to cool to room temperature, water (5 mL) and hexanes (3 mL) were added. The mixture was vigorously shaken for extraction into the hexane phase, which was then filtered through a short silica gel plug. Analysis of the filtrate by $^{19}F$ NMR indicated the formation of fluorobenzene. The characteristic multiplet at −114 ppm was identical with that observed for an authentic sample of fluorobenzene (Aldrich).

Example 3

A mixture of 2-bromonaphthalene (0.08 g), copper (II) fluoride (0.04 g), TMEDA (0.31 mL), and HMPA (1.5 mL) was vigorously stirred at 180° C. for 3 hrs. After the mixture was allowed to cool to room temperature, water (5 mL) and hexanes (2 mL) were added. The mixture was vigorously shaken for extraction into the hexane phase, which was then filtered through a short silica gel plug. Analysis of the filtrate by $^{19}$F NMR indicated the formation of 2-fluoronaphtalene. The characteristic multiplet at –116 ppm was identical with that observed for an authentic sample of 2-fluoronaphtalene (Aldrich).

Example 4

A mixture of 2-iodonaphthalene (0.10 g), copper (II) fluoride (0.04 g), TMEDA (0.31 mL), and sulfolane (1.5 mL) was vigorously stirred at 180° C. for 9.5 hrs. After the mixture was allowed to cool to room temperature, water (5 mL) and hexanes (2 mL) were added. The mixture was vigorously shaken for extraction into the hexane phase, which was then filtered through a short silica gel plug. Analysis of the filtrate by $^{19}$F NMR indicated the formation of 2-fluoronaphtalene. The characteristic multiplet at –116 ppm was identical with that observed for an authentic sample of 2-fluoronaphtalene (Aldrich).

What is claimed is:

1. A fluorination process, comprising:
   contacting a compound having an unactivated aryl group substituted with one or more of X, wherein X is I, Br, Cl, triflate, or tosylate with:
   a) a source of fluoride or bifluoride,
   b) a transition metal, and
   c) a ligand;
   wherein the contacting is carried out in a solvent for a time sufficient to replace one or more of X with F.

2. The process of claim 1 wherein the aryl group is substituted with optionally substituted aryl, hydrogen, optionally substituted alkyl, aryloxy, alkoxy, amine, and hydroxyl.

3. The process of claim 1 wherein the aryl group is benzene or naphthalene, optionally substituted with one or more of bromo and iodo.

4. The process of claim 1 wherein the source of fluoride or bifluoride is selected from the group consisting of NaF, KF, RbF, CsF, AgF, TlF, NaHF$_2$, and KHF$_2$.

5. The process of claim 1 wherein the transition metal is selected from the group consisting of Cu, Ag, Au, Fe, Co, Ni, Ru, Rh, Pd, Os, Ir, Pt, and Re.

6. The process of claim 1 wherein the ligand is selected from the group consisting of N,N,N',N'-tetramethylethylenediamine, N,N,N',N'-tetraethylethylenediamine, and N,N,N',N'-tetramethylphenylenediamine.

7. The process of claim 1 wherein the solvent is selected from the group consisting of hexamethylphosphoramide, tetramethylene sulfone, N-methyl-2-pyrrolidone, and diglyme.

8. The process of claim 1 wherein the solvent is an aprotic solvent.

* * * * *